US 10,130,538 B2

(12) United States Patent
Toms et al.

(10) Patent No.: US 10,130,538 B2
(45) Date of Patent: Nov. 20, 2018

(54) PNEUMATIC MATTRESS

(71) Applicant: LINET SPOL S.R.O., Slany (CZ)

(72) Inventors: Martin Toms, Hampshire (GB); Brian Frank Pile, Fareham (GB); Ian Malcolm Ryall, Waterlooville (GB)

(73) Assignee: LINET SPOL S.R.O., Slany (CZ)

( * ) Notice: Subject to any disclaimer, the term of this patent is extended or adjusted under 35 U.S.C. 154(b) by 38 days.

(21) Appl. No.: 14/398,544

(22) PCT Filed: Apr. 29, 2013

(86) PCT No.: PCT/IB2013/001013
§ 371 (c)(1),
(2) Date: Nov. 3, 2014

(87) PCT Pub. No.: WO2013/164688
PCT Pub. Date: Nov. 7, 2013

(65) Prior Publication Data
US 2015/0089748 A1    Apr. 2, 2015

Related U.S. Application Data

(60) Provisional application No. 61/645,879, filed on May 11, 2012.

(30) Foreign Application Priority Data

May 3, 2012    (GB) ................... 1207838.2

(51) Int. Cl.
*A61G 7/057* (2006.01)
*A61F 5/34* (2006.01)

(52) U.S. Cl.
CPC ............ *A61G 7/05776* (2013.01); *A61F 5/34* (2013.01); *A61G 7/05769* (2013.01); *A61G 7/05784* (2016.11)

(58) Field of Classification Search
CPC .. A61G 7/05776; A61G 7/00; A61G 7/05769; A61G 2007/05784; A61G 13/04;
(Continued)

(56) References Cited

U.S. PATENT DOCUMENTS 3,486,177 A * 12/1969 Marshack .................... 5/726
5,109,506 A    5/1992 Uetake
(Continued)

FOREIGN PATENT DOCUMENTS

| EP | 2324808 A1 | 5/2011 |
|----|------------|--------|
| GB | 1483045 A | 8/1977 |
| WO | 2010058158 A1 | 5/2010 |

OTHER PUBLICATIONS

European Patent Office, International Search Report for International Application No. PCT/IB2013/001013 filed Apr. 29, 2013, dated Apr. 9, 2013.
(Continued)

*Primary Examiner* — Eric J Kurilla
*Assistant Examiner* — Amanda L Bailey
(74) *Attorney, Agent, or Firm* — Thedford I. Hitaffer; Hitaffer & Hitaffer, PLLC

(57) ABSTRACT

A pneumatic mattress having a plurality of pneumatic cells so connected that sets of them can be selectively and cyclically pressurized and exhausted in sequence to support a user, or permanently inflated. The mattress also including an air flow manifold within a cover around the cells for providing air flow to spaces between some of the pneumatic cells beneath of the cover. The cells are provided transversely of the mattress with longitudinal edge cells, and the air flow manifold is provided inwards of the longitudinal cells across the ends of the transverse cells. The cover is semi-permeable to allow moisture from the patient to be carried away by the air flow. Between the cells and the cover,
(Continued)

Figure 1:
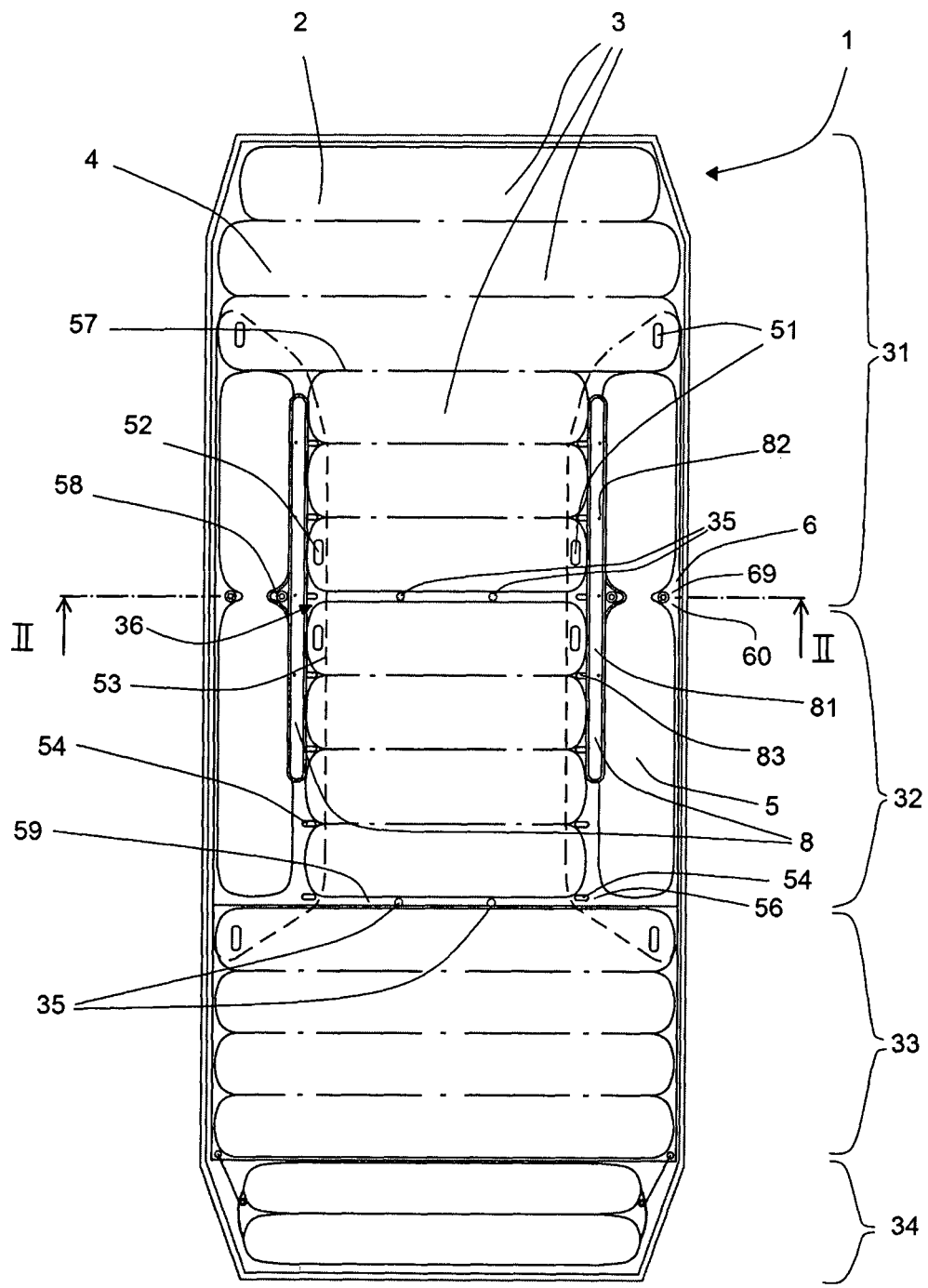

a replaceable open weave or gauze layer of non-woven material is provided, allowing air flow from one inter-cell space to the next with the cover held from the cells by the gauze layer.

21 Claims, 2 Drawing Sheets

(58) Field of Classification Search
CPC ........ A61G 7/005; A61G 7/015; A61G 13/08; A61F 5/34; A61F 5/00
See application file for complete search history.

(56) References Cited

U.S. PATENT DOCUMENTS

| | | | |
|---|---|---|---|
| 5,375,273 A * | 12/1994 | Bodine et al. | 5/710 |
| 5,640,728 A | 8/1997 | Graebe | |
| 5,699,570 A * | 12/1997 | Wilkinson et al. | 5/713 |
| 5,966,762 A * | 10/1999 | Wu | A61G 7/05769 5/615 |
| 6,216,299 B1 * | 4/2001 | Kohlman | A61G 5/1043 5/654 |
| 6,371,976 B1 * | 4/2002 | Vrzalik et al. | 607/104 |
| 6,829,796 B2 * | 12/2004 | Salvatini et al. | 5/713 |
| 7,945,979 B1 | 5/2011 | Lin | |
| 2005/0120483 A1 | 6/2005 | Clapper | |
| 2006/0282955 A1 * | 12/2006 | Gilchrest et al. | 5/732 |
| 2007/0101504 A1 * | 5/2007 | Gilchrest et al. | 5/706 |
| 2011/0302719 A1 | 12/2011 | Schwirian | |

OTHER PUBLICATIONS

European Patent Office, International Preliminary Report on Patentability for International Application No. PCT/IB2013/001013 filed Apr. 29, 2013, dated Jul. 15, 2014.

* cited by examiner

PNEUMATIC MATTRESS

CROSS-REFERENCE TO RELATED APPLICATIONS

This application, filed under 35 USC 371, is a United States National Stage Application of International Application No. PCT/IB2013/001013, filed Apr. 29, 2013, which claims priority to U.S. Provisional Application No. 61/645,879, filed May 11, 2012 and UK Application No. GB 1207838.2, filed on May 3, 2012, the disclosures of which are incorporated herein by reference.

The present invention relates to a pneumatic mattress.

We have filed a number of patent applications in respect of a type of pneumatic mattress, which has a plurality of pneumatic cells so connected that sets of them can be selectively and cyclically pressurised and exhausted—or inflated and deflated—in sequence to support a user, normally a patient liable to suffer or actually suffering from pressure sores. Cycling the mattress simulates movement that a patient would make if fit and healthy so as to avoid supporting his/her weight in the same place all the time.

In certain markets constant pressure pneumatic mattresses are preferred. In such a mattress the pneumatic cells are all constantly inflated. To enable them to adapt to the shape of a patient lying on them, air is allowed to escape from the cells via a series of small perforations. This has the advantage of providing air flow to the underside of the mattress cover, which can be advantageous in keeping the patient and his/her wounds and skin dry.

For a variety of reasons, we prefer to use a cell arrangement which differs from the normal constant pressure cell arrangement. Our arrangement does not lend itself to use of the bleeds holes. Indeed we feel that use of constant pressure cells that can collapse to the conventional extent is not ideal. Nevertheless we believe that the air flow from the bleed perforations is advantageous.

The object of the present invention is to provide an improved pneumatic mattress.

According to the invention there is provided a pneumatic mattress having a plurality of imperforate cells within a cover and means for providing air to flow to spaces between at least some of the individual cells beneath the cover.

Whilst the individual cells having the air flow between them could extend longitudinally of the mattress, we prefer to arrange them transversely of the mattress. Additionally, we prefer to provide a longitudinal edge cells. With such a cell arrangement, we can provide air flow manifolds inwards of the longitudinal cells across the ends of the transverse cells.

Conveniently the manifolds are readily bendable, with the edge cells being necked in alignment with a junction between two of the transverse cells, whereby the mattress can be bent for inclination of a torso portion to lift the patient to a sitting position, with the air flow being provided to both a seat portion and a torso portion of the mattress.

For a purpose disclosed in our co-pending application of even date, the cells are preferably tethered at the neck.

Preferably, the cells are covered by a semi-permeable cover, which allows moisture through from the patient to be carried away by the air flow. Between the cells and the cover, a replaceable open weave or gauze layer of non-woven material, allowing airflow from one inter-cell space to the next with the cover held from the cells by the gauze layer.

Figure 2:
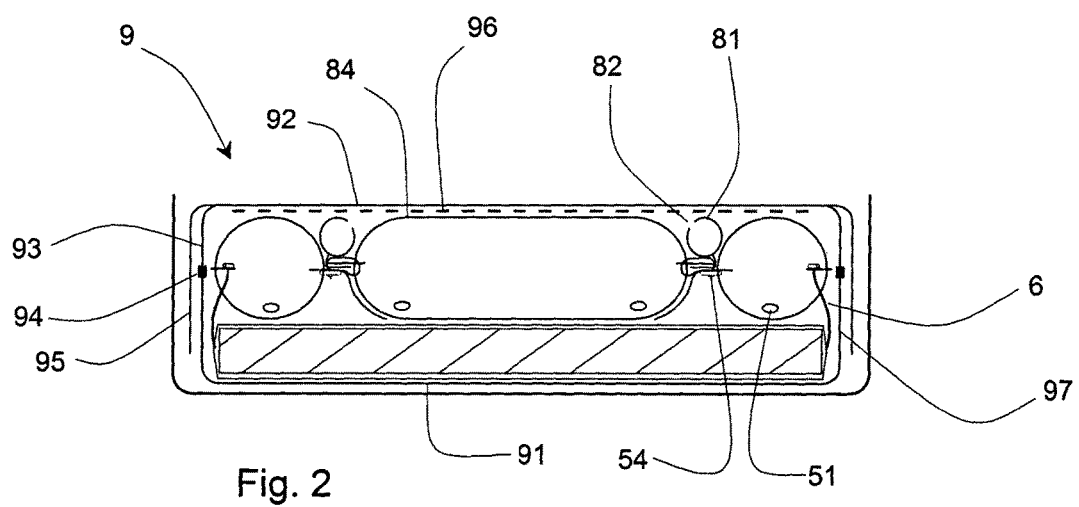

To help understanding of the invention, a specific embodiment thereof will now be described by way of example and with reference to the accompanying drawings, in which:

FIG. 1 is a plan view of a mattress according to the invention with the top sheet of a mattress cover removed and FIG. 2 is a transverse cross-sectional end view of the mattress of FIG. 1 on the line II-II in FIG. 1.

Referring to the drawings, a pneumatic mattress 1 is comprised primarily of a single layer 2 of transverse pneumatic cells 3. These are provided as four groups, a head and torso group 31, a seat and upper leg group 32, a lower leg group 33, and a heel group 34. The groups are pneumatically separate from each other, in that all the cells within each group are pneumatically interconnected and separately supplied with inflation air, by a non-shown pump, which performs no function in the invention save providing pumped air. The exception from the pneumatic interconnection is in the heel group which has a manual control for inflating either, both or neither of the heel group cells, for extending the mattress from a shorter to a longer length or vice versa. The cells within the groups are integral in that they are formed from the same two layers of polymeric material welded together to provide the cells and their pneumatic connection. The groups are distinct and detachably connected together as follows:

group 31 being clipped with pop fasteners 35 to group 32;
group 32 being clipped with pop fasteners 35 to group 33; and
group 33 being strapped to group 34 as explained in more detail below.

Two out of three of the head cells 4 in the group 31 and the cells of the groups 33 are full width, with the other transverse cells being shorter. The heel cells are some 10% shorter. Along the mattress, across the ends of the other shorter cells, i.e. in the groups 31, 32, two sides cells 5 extend. These are connected in two ways to the neighbouring cells. Firstly, air connectors 51 on the underside of certain cells in the groups 31,32,33 are passed through dumbbell slots 52 in margins 53 of the side cells.

Secondly, loop connections 54 are made between individual cells in the groups 31,32,33 and corresponding apertures 56 in the margins 53. These are connected at 57 to the head cell adjoining the torso cells, at 58 to the junction between the torso cells and the seat cells and at 53 to the lower leg cell adjacent the torso group. The side cells are necked at 58, providing in conjunction with the junction of the cells 31,32 a bend region 36 for the upper layer. Here the pneumatic cells as a whole are connected by tethers 6 to a lower layer 7 of the mattress.

In accordance with the invention, air supply manifolds 8 extend at both sides of the mattress between the side cells 5 and the cell groups 32,33. They are formed in the same manner as that the cells, that is of two welded layers of polymer sheet. They are clipped to the cells by the loop connectors 54. In their sheets 81 facing inwards of the mattress, they are provided with perforations 82, at positions corresponding to spaces 83 between the upper portions 84 of the cells.

The mattress has a cover 9, comprised of
a lower sheet 91 with an up-turned edge 92,
a top sheet 92 with a down turned edge 93,
a sliding clasp fastener 94 jointing the two edges,
a skirt 95 from the top sheet covering the fastener,
an open-weave, non-woven layer 96 separate from the top sheet and clipped to opposite end one of the cells.

The top sheet is or semi-permeable/breathable fabric through which moisture from a patient can pass inside the cover.

With the cells inflated, the top cover evenly laid on the cells and air being to pumped to the manifolds 8, there is air flow inwards between the individual ones of the torso and upper leg cells, in the spaces 83. Insofar as this flow is from both ends of the spaces, it leaves them longitudinally of the mattress via the open weave layer 96 and any local lifting that there may be of this layer from the tops of the cells.

In use with a patient laid on the mattress, the top sheet and the open weave layer are locally pressed onto the cells by the patient's body. The body's weight is supported by the pressure in the cells times the surface area of the cells flattened to support the body. The pressure is set for the body weight such that there is some space 83 remaining between individual cells. Air flows here, drawing away with it moisture permeating through the top sheet of the cover and passing through the open-weave layer to the spaces. In certain areas, such as under the patient's back, some flow will occur through the open weave layer.

The invention is not intended to be restricted to the details of the above described embodiment. For instance, it is envisaged that the torso and seat/upper-legs cells could run longitudinally. In which case the air flow manifolds could be arranged transversely across the ends of such longitudinal cells.

Further it would be possible to replace the manifolds as such with a series of open-ended tubes extending into the inter-cell spaces and directing air flow into the spaces. Insofar as the spaces taper to non-existence at the cells mid-height, the tubes would need to be supported at a position not to high nor not too low in the spaces, to avoid their closure by local weight of the patient. Nevertheless, it can be envisaged that such tubes could be provided with perforations along their length allowing for distribution of air flow into the spaces. The tubes could be conventional circular cross-section tubes or welded on pockets extending the length of the tubes. Such cell long tubes of whichever type could be supplied with air flow from either or both ends.

The invention claimed is:

1. A pneumatic mattress having a plurality of individual, imperforate cells within a cover, with air flowing to spaces between at least some of the individual, imperforate cells beneath the cover, wherein:
    the imperforate cells include
        transverse cells arranged transversely of the mattress,
        longitudinal edge cells provided across ends of the transverse cells and
        the longitudinal edge cells detachably connected to the transverse cells, and wherein
    the transverse cells are between the longitudinal edge cells are divided into two groups including a first group of cells and a second group of cells, the cells in each of the two groups being integrated and the groups being detachably connected to one another, and
    the longitudinal edge cells are necked only in alignment with a junction between two of the transverse cells, whereby the mattress can be bent for inclination of the first group of cells, with manifolds to provide air flow to both the first and second groups of cells of the mattress, and
    the manifolds further providing air flow to spaces between the longitudinal edge cells and ends of the transverse cells, the manifolds being provided inwards of the longitudinal edge cells and across the ends of the transverse cells; and wherein
    the manifolds
        extend between the longitudinal edge cells and the transverse cells of both the first and the second cell groups, and
        are connected to the transverse cells and the longitudinal edge cells by a detachable connection, and
        have inwardly directed air perforations at positions corresponding to the spaces between upper portions of each of the two groups of cells for directing air to the spaces.

2. A pneumatic mattress according to claim 1, wherein the manifolds are bendable.

3. A pneumatic mattress according to claim 2, wherein the manifolds are provided at sides of the mattress inwards of the longitudinal edge cells.

4. A pneumatic mattress according to claim 1, wherein the longitudinal edge cells are necked at necks and the longitudinal edge cells are tethered at the necks.

5. A pneumatic mattress according to claim 1, wherein the cover is a semi-permeable cover.

6. A pneumatic mattress as claimed in claim 5, further including a replaceable open weave or gauze layer of non-woven material between the longitudinal edge cells and the transverse cells and the cover, allowing airflow from one of the spaces to a next one of the spaces with the cover held from the longitudinal edge cells by the replaceable open weave or gauze layer.

7. A pneumatic mattress according to claim 1, wherein the mattress has further transverse cells extending a full width of the mattress at head and foot ends of the mattress.

8. A pneumatic mattress as claimed in claim 1, wherein the mattress has further transverse cells extending a substantial width of the mattress at head and foot ends of the mattress.

9. A pneumatic mattress as claimed according to claim 1, wherein the longitudinal edge cells are longer than the manifolds.

10. A pneumatic mattress according to claim 1, wherein the manifolds are provided at sides of the mattress inwards of the longitudinal edge cells.

11. A pneumatic mattress having a plurality of individual imperforate cells within a cover, with air flowing to spaces between at least some of the individual, imperforate cells beneath the cover, wherein:
    the imperforate cells include
        transverse cells arranged transversely of the mattress,
        longitudinal edge cells provided across ends of the transverse cells
        the longitudinal edge cells and the transverse cells being on substantially a same horizontal plane, and
    the longitudinal edge cells detachably connected to the transverse cells, and wherein
    the transverse cells are provided between the longitudinal edge cells and are divided into two groups including a first group of cells and a second group of cells, the cells in each of the two groups being integrated and the groups being detachably connected to one another, and
    the longitudinal edge cells have a reduced diameter portion only in alignment with a junction between two of the transverse cells, whereby the mattress can be bent for inclination of the first group of cells, with manifolds to provide air flow to both the first and second groups of cells of the mattress, and
    the manifolds for further providing air flow to spaces between the longitudinal edge cells and ends of the transverse cells, the manifold being provided inwards of the longitudinal edge cells and across the ends of the transverse cells; and wherein
    the manifolds extend between the longitudinal edge cells and the transverse cells of both the first and second cell groups, and are connected to the transverse cells and the longitudinal edge cells by a detachable connection, and have inwardly directed air perforations at positions corresponding to portions of the spaces between upper portions of each of the two groups of cells for directing air to the spaces.

12. A pneumatic mattress as claimed in claim 11, wherein the manifolds are readily bendable.

13. A pneumatic mattress as claimed in claim 12, wherein the manifolds are provided at sides of the mattress inwards of the longitudinal edge cells.

14. A pneumatic mattress according to claim 11, wherein the longitudinal edge cells are necked at necks and the longitudinal edge cells are tethered at the necks.

15. A pneumatic mattress according to claim 11, wherein the cover is a semi-permeable cover.

16. A pneumatic mattress as claimed in claim 15, further including a replaceable open weave or gauze layer of non-woven material between the longitudinal edge cells and the transverse cells and the cover, allowing airflow from one of the spaces to a next one of the spaces with the cover held from the longitudinal edge cells and the transverse cells by the replaceable open weave or gauze layer.

17. A pneumatic mattress according to claim 11, wherein the mattress has further transverse cells extending a full width of the mattress at head and foot ends of the mattress.

18. A pneumatic mattress as claimed in claim 11, wherein the mattress has further transverse cells extending a substantial width of the mattress at head and foot ends of the mattress.

19. A pneumatic mattress as claimed according to claim 11, wherein the longitudinal edge cells are longer than the manifolds.

20. A pneumatic mattress according to claim 11, wherein the manifolds are provided at sides of the mattress inwards of the longitudinal edge cells.

21. A pneumatic mattress having a plurality of individual, imperforate cells within a cover, with air flowing to spaces between at least some of the individual, imperforate cells beneath the cover, wherein:

the imperforate cells are pneumatic cells including transverse cells arranged transversely of the mattress, wherein the transverse cells have a thickness that is substantially uniform;

longitudinal edge cells provided across ends of the transverse cells, wherein the longitudinal edge cells and the transverse cells are on substantially a same horizontal plane, and the longitudinal edge cells detachably connected to the transverse cells, and wherein the transverse cells are between the longitudinal edge cells are divided into two groups including a first group of cells and a second group of cells, the cells in each of the two groups being integrated and the groups being detachably connected to one another, and the longitudinal edge cells are necked only in alignment with a junction between two of the transverse cells, whereby the mattress can be bent for inclination of the first group of cells, with manifolds to provide air flow to both the first and second groups of cells of the mattress, and the manifolds further providing air flow to spaces between the longitudinal edge cells and ends of the transverse cells, the manifolds being provided inwards of the longitudinal edge cells and across the ends of the transverse cells; and wherein the manifolds extend between the longitudinal edge cells and the transverse cells of both the first and the second cell groups, and are connected to the transverse cells and the longitudinal edge cells by a detachable connection, and have inwardly directed air perforations at positions corresponding to the spaces between upper portions of each of the two groups of cells for directing air to the spaces.

* * * * *